(12) United States Patent
McAtamney et al.

(10) Patent No.: US 7,618,377 B2
(45) Date of Patent: Nov. 17, 2009

(54) GALVANIC ISOLATION OF A MEDICAL APPARATUS

(75) Inventors: Michael D. McAtamney, Navan (IE); Jim J. Shortt, Trim (IE); Rudolf P. Ruizenaar, Delft (NL); John P. Kroetz, Rochester, NY (US); Daniel R. Sommers, Skaneateles, NY (US); John A. Melquist, Skaneateles, NY (US); Alexius O. Looije, Naaldwijk (NL)

(73) Assignee: Welch Allyn, Inc., Skaneateles Falls, NY (US)

( * ) Notice: Subject to any disclaimer, the term of this patent is extended or adjusted under 35 U.S.C. 154(b) by 581 days.

(21) Appl. No.: 11/238,233

(22) Filed: Sep. 29, 2005

(65) Prior Publication Data

US 2007/0073175 A1 Mar. 29, 2007

(51) Int. Cl.
*A61B 5/02* (2006.01)
(52) U.S. Cl. ..................... 600/508; 600/300
(58) Field of Classification Search .......... 600/382, 600/508, 509, 300, 301, 379, 411; 128/908; 439/91, 729, 909, 602
See application file for complete search history.

(56) References Cited

U.S. PATENT DOCUMENTS

| | | | |
|---|---|---|---|
| 4,280,507 A | * | 7/1981 | Rosenberg .............. 600/508 |
| 4,440,172 A | | 4/1984 | Langer |
| 4,850,356 A | | 7/1989 | Heath |
| 5,046,968 A | | 9/1991 | Baur et al. |
| 5,181,864 A | | 1/1993 | Wakino et al. |
| 5,341,812 A | | 8/1994 | Allaire et al. |
| 5,546,950 A | | 8/1996 | Schoeckert et al. |
| 5,582,180 A | | 12/1996 | Manset et al. |
| 5,599,208 A | | 2/1997 | Ward |
| 5,713,925 A | | 2/1998 | Sullivan et al. |
| 6,062,902 A | * | 5/2000 | Buckles et al. .............. 439/502 |
| 6,623,312 B2 | * | 9/2003 | Merry et al. ................. 439/729 |
| D535,029 S | * | 1/2007 | McAtamney et al. ...... D24/167 |

* cited by examiner

*Primary Examiner*—Carl H Layno
*Assistant Examiner*—Brian T Gedeon
(74) *Attorney, Agent, or Firm*—Hiscock & Barclay, LLP; R. Stephen Rosenholm

(57) ABSTRACT

A medical device, such as an electrocardiogram (ECG) monitoring apparatus, provides galvanic isolation between low voltage electronics and a plurality of externally exposed ECG (patient contact) lead wires and electrodes. The ECG lead wires and/or electrodes can potentially make unwanted contact with sources of high voltage, such as from defibrillation devices. The defibrillation pulses can cause damage to the low voltage electronics within the ECG monitoring apparatus. Electrical resistance is provided outside of the ECG lead wires and electrodes and separate from the low voltage electronics to protect against misdirection of a defibrillation pulse towards the low voltage electronics, and to protect against misdirection of a defibrillation pulse away from the patient for which the benefit of the defibrillation pulse is intended.

20 Claims, 4 Drawing Sheets

GALVANIC ISOLATION OF A MEDICAL APPARATUS

CROSS-REFERENCE TO APPLICATIONS INCLUDING RELATED SUBJECT MATTER

This application includes subject matter that is related to subject matter included within U.S. design Pat. application Serial No. 29/217,149, filed Nov. 12, 2004.

FIELD OF THE INVENTION

This invention relates generally to an apparatus that is configured to provide galvanic isolation between low voltage electronics and a plurality of externally exposed lead wires and electrodes that can potentially make contact with sources of high voltage, and in particular to a medical apparatus, such as an electrocardiogram (ECG) monitoring apparatus, that is configured to provide galvanic isolation between low voltage electronics and a plurality of externally exposed lead wires and electrodes that can potentially make contact with sources of high voltage, such as defibrillation pulses.

BACKGROUND OF THE INVENTION

Medical devices are typically operated inside of a health care environment in close proximity to patients, other electrical devices and other objects made of conductive material. As a result, there is a risk of unwanted transfer of electrical energy between such devices and such objects while providing health care to a patient.

For example, an electrocardiogram (ECG) monitoring apparatus is a medical device that receives and processes electrocardiogram (ECG) signals generated by a circulatory system of a person. The apparatus typically includes a plurality of ECG (patient contact) electrodes that are each electrically connected to a lead wire and that are each configured to make physical contact with the person being monitored. The ECG electrodes and lead wires are also configured to receive and relay ECG signals generated by the person to components of the ECG monitoring apparatus that process the ECG signals.

In some circumstances, the person may be experiencing some sort of cardiovascular instability, such as ventricular fibrillation. Ventricular fibrillation is a disturbance of electrical activity within a ventricular muscle of the heart. In order to arrest ventricular fibrillation, the patient may be administered a defibrillation shock via defibrillating device. In some circumstances, the patient may be administered the defibrillation shock while the patient is being monitored by an ECG monitoring apparatus. The defibrillation shock can create a voltage surge that can unintentionally conduct (travel) through one or more of the ECG contact electrodes and/or lead wires and can cause damage to the components of the ECG monitoring apparatus that process those ECG signals.

SUMMARY OF THE INVENTION

The invention provides for a method and apparatus for providing galvanic isolation between a medical device and other sources of electrical energy within a health care environment. In one embodiment, the invention provides for an electrocardiogram (ECG) monitoring apparatus and method that provides improved galvanic isolation between low voltage electronics that process ECG signals and a plurality of externally exposed ECG (patient contact) electrodes and lead wires that receive and relay the ECG signals to the low voltage electronics.

An electrical resistance is provided that corresponds to each of a plurality of external and detachable ECG (patient contact) lead wires and electrodes. Each ECG (patient contact) lead wire is configured to electrically connect to and include an ECG (patient contact) electrode. Each ECG (patient contact) electrode is configured to attach to a patient.

In accordance with the invention, the electrical resistance is provided outside of the ECG lead wires and electrodes and separate from the low voltage electronics. The electrical resistance is preferably implemented as a galvanically shielded resistor that is located in series between the low voltage electronics and a corresponding ECG lead wire. The electrical resistance protects the low voltage electronics against the occurrence of a high voltage surge (defibrillation pulse), conducted through an ECG (patient contact) electrode and or lead wire. Also, the electrical resistance protects against misdirection of a defibrillation pulse away from the patient for which the benefit of the defibrillation pulse is intended.

Preferably, each ECG (patient contact) lead wire is electrically connected in series with the galvanically shielded resistor. In this type of embodiment, each ECG (patient contact) lead wire and/or electrode is simpler and less expensive to manufacture. Failure of a (patient contact) lead wire and/or electrode does not require repair or replacement of a corresponding resistor and failure of a resistor does not require repair or replacement of a corresponding ECG contact electrode and/or lead wire.

Optionally, a cavity encloses and provides mechanical support to the resistor and is dimensioned to accommodate a variety of resistor sizes. As a result, the manufacture of the ECG monitoring apparatus is flexible with respect to the selection and incorporation of a particular resistor among various types and sources of resistors.

BRIEF DESCRIPTION OF THE DRAWINGS

The objects and features of the invention can be better understood with reference to the claims and drawings described below. The drawings are not necessarily to scale, and emphasis is instead generally being placed upon illustrating the principles of the invention. In the drawings, like reference numbers are used to indicate like parts throughout the various views. Differences between like parts may cause those parts to be indicated by different reference numbers. Unlike parts are indicated by different reference numbers.

DETAILED DESCRIPTION OF THE INVENTION

Figure 1A:
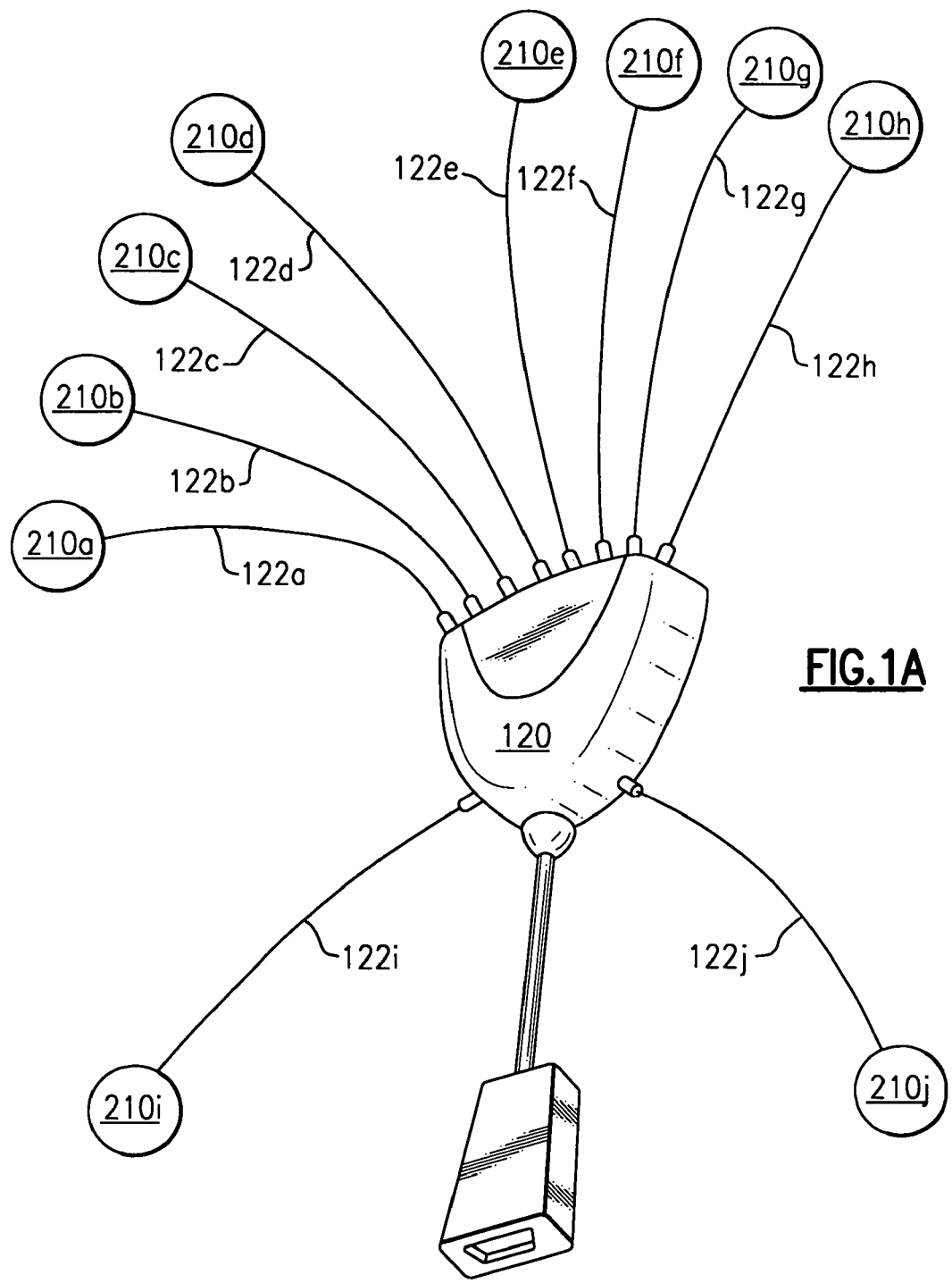
FIG. 1A is a top view of an embodiment of an ECG monitoring apparatus including ten patient contact lead wires and electrodes that are configured to attach to a patient.

FIG. 1A is a top conceptual view of an embodiment of an ECG monitoring apparatus 120 including (10) ECG patient contact lead wires 122a-122j that include patient contact electrodes 210a-210j and that are configured to be attached to a person, also referred to as a patient. When the ECG lead wires 122a-122j are attached to the patient, the ECG signals generated by the patient (not shown) are received by the patient contact lead wires 122a-122j and processed by the ECG monitoring apparatus 120. The (8) ECG lead wires 122a-122h are configured to make contact with the upper body (chest and arms) of the patient. The (2) lead wires 122i-122j are configured to make contact with the lower body (legs) of the patient.

In some circumstances, the patient may be administered a defibrillation shock (voltage surge), of typically about 2000 volts while being monitored by the ECG monitoring apparatus 120. In some circumstances, a defibrillation shock can arrest instabilities of cardio activity occurring within the patient.

Figure 2:
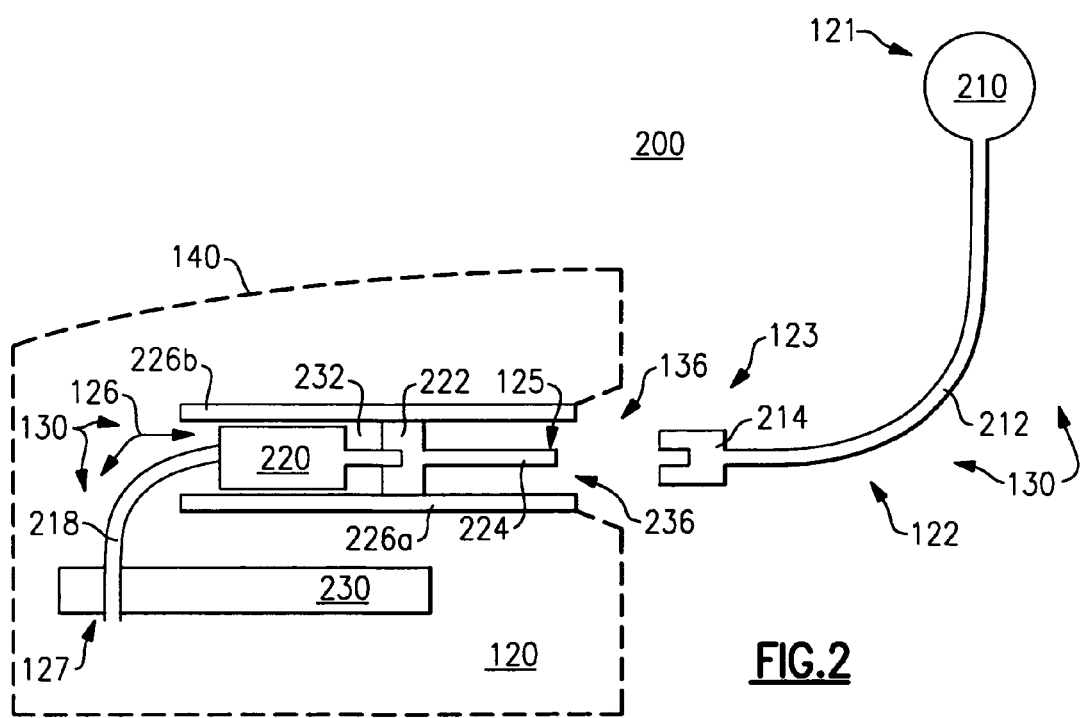
FIG. 2 illustrates a side cross-sectional view of a conductive pathway within a passageway of the ECG monitoring apparatus of FIGS. 1A-1B.

In this type of circumstance, a voltage surge associated with the defibrillation shock can unintentionally conduct (travel) through one or more of the patient contact lead wires 122a-122j and cause damage to low voltage electrical circuits located within the ECG monitoring apparatus 120 (See FIG. 2). The voltage surge (energy) associated with the defibrillation shock is intended to be directed towards the patient in order to provide therapy to the patient. Objects that are in contact with or proximate to the patient can potentially cause the voltage surge (energy) of the defibrillation shock to conduct away from the patient, and cause the patient to be denied the benefit of the intended therapy. Consequently, a defibrillation voltage surge should not be allowed to travel away from the patient and towards the electronic circuitry of the ECG monitoring device 120.

To function properly, portions of electronic circuitry residing within the ECG monitoring apparatus 120 that are vulnerable to a voltage surge should be protected from the detrimental effects of a voltage surge. Accordingly, embodiments of the invention provide for galvanic isolation of vulnerable portions of electronic circuitry residing within the ECG monitoring apparatus 120.

Figure 1B:
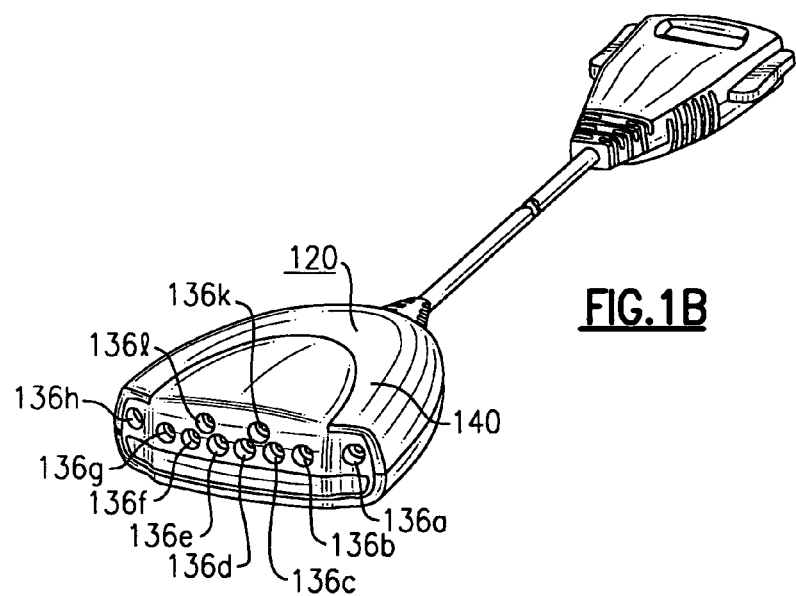
FIG. 1B is a frontal view of the ECG monitoring apparatus of FIG. 1A.

FIG. 1B is a frontal view of an outer surface 140 the ECG monitoring apparatus 120 of FIG. 1A. As shown, a frontal side of the ECG monitoring apparatus 120 includes a lower row of (8) openings 136a-136h of passageways 236a-236h (See FIGS. 2, 3A) and an upper row of (2) openings 136k-361l of passageways 236k-236l (See FIGS. 2, 3B). The lower row of openings 136a-136h are configured to receive ECG patient contact lead wires 122a-122h. The upper row of openings 136k-136l are configured to receive audio sensor cables (not shown). A rear side (not shown) of the ECG monitoring apparatus 120 includes (2) openings (not shown) of passageways receiving ECG patient contact lead wires 122i-122j.

FIG. 2 illustrates a side cross-sectional view 200 of a passageway 236 within the ECG monitoring apparatus of FIGS. 1A-1B. The passageway 236 includes a rear conductive (electronics side) pathway 126 that includes electrical components that are electrically connected in series. A front conductive (patient side) pathway 122, shown as located outside of the apparatus 120, also includes electrical components that are electrically connected in series. The front conductive (patient side) pathway 122 is attachable to and detachable from the rear conductive (electronics side) pathway 126. A combined conductive pathway 130 represents the combination of the front conductive pathway 122 and the rear conductive pathway 126 when electrically attached to each other. As shown, the front conductive (patient side) pathway 122 is detached from the rear conductive (electronics side) pathway 126.

The front conductive (patient side) pathway 122, representing an individually detachable and replaceable ECG (patient contact) lead wire 122, includes at a first end 121 and a second end 123, an ECG (patient contact) electrode 210, an insulated conductor 212 and an electrical connector 214. The patient contact electrode 210 is located at the first end 121 of the front conductive pathway 122 and is electrically connected to an insulated conductor 212. The insulated conductor 212 is also electrically connected to a female type of electrical connector 214 that is located at the second end 123 of the front conductive pathway 122. A female type of electrical connector is less likely to make unwanted electrical contact with outside voltage sources.

The rear conductive (electronics side) pathway 126 includes a first end 125 and a second end 127, a contact pin 224, a base 222, a resistor 220 and a conductor 218. The contact pin 224 is located at the first end 125 of the rear conductive pathway 126 and is recessed within the passageway 236 in order to avoid accidental electrical contact with anything other than a patient contact lead wire 122.

The contact pin 224 is also configured to make electrical contact with a resistor 220. The resistor 220 is configured to make electrical contact with a conductor 218 that is configured to make electrical contact with a printed circuit board (PCB) 230 at the second end 127 of the rear conductive pathway 126. The contact pin 224 is configured to physically and electrically engage the connector 214 in order to electrically attach the front conductive pathway 122 to the rear conductive pathway 126.

The printed circuit board (PCB) 230 includes low voltage electronic components that can be damaged as a result of receiving a voltage surge traveling through the combined conductive pathway 130. The resistor 220 is located in series between the first end 125 and the second end 127 of the rear conductive pathway 126 and is configured to provide substantial electrical protection to the PCB 230 from such a voltage surge. The resistor 220 is configured to reduce a voltage at locations between the resistor 220 and the second end 127 of the rear conductive pathway 126 relative to a voltage located at the first end 125 of the rear conductive pathway 126. Preferably, the resistor provides 10 kilo-ohms of electrical resistance.

The resistor 220 delimits the rear conductive (electronics side) pathway 126 into a higher voltage portion and a lower voltage portion. The higher voltage portion includes the contact pin 224, the base 222 and the resistor 220. A lower voltage portion of the rear conductive pathway 126 includes the conductor 218 that is located downstream of the voltage reducing resistor 220.

A lower carrier 226a and an upper carrier 226b are internal structures 226a-226b that bound the passageway 236 that substantially surround at least the higher voltage portion of the rear conductive pathway 126. Preferably, the carriers 226a-226b also substantially surround the electrical connector 214 of the front conductive (patient side) pathway 122, as shown.

The carriers 226a-226b, as internal structures 226a-226b of the ECG monitoring apparatus 120, are configured to provide mechanical support and electrical (galvanic) isolation to at least the higher voltage portion of the rear conductive (electronics side) pathway 126. Encapsulating the higher voltage portion, such as the contact pin 224, within the passageway 236, helps prevent accidental contact between the contact pin 224 and an outside object of higher electrical potential.

A vertical baffle (not shown in FIG. 2) forms a portion of an inner surface of the passageway 236 and is located in opposite horizontal directions (each side), as opposed to opposite vertical directions (above and below), the rear conductive pathway 126 (See FIG. 3A). The vertical baffle is formed from abutting (stacking) the lower carrier 226a and the upper carrier 226b together (Shown in FIG. 2B). Each vertical baffle provides additional galvanic isolation between high voltage potions of adjacent pathways 236.

In accordance with the invention, notice that the front conductive (patient side) pathway (ECG patient contact lead wire) 122 excludes a resistor. As a result, the front conductive pathway (ECG patient contact lead wire) 122 includes less components and is easier and less expensive to manufacture than an ECG lead wire that includes a resistor.

Further, a failure of the resistor 220 located within the combined conductive pathway 130 does not require repair or replacement of a corresponding ECG (patient contact) lead wire 122. Likewise, failure of an ECG lead wire 122 does not require replacement of a resistor 220 within the conductive pathway 130 within which the resistor 220 is located. Essentially, the resistor 220 is salvageable if the corresponding ECG lead wire 122 fails and the ECG lead wire is salvageable if the corresponding resistor 220 fails.

In accordance with the invention, neither is a resistor located within or near the low voltage electronics. Each high voltage portion of a conductive pathway 130 is required to be located a minimum distance from other high voltage portions of other conductive pathways 130. For example, some printed circuit board (PCB) designs require high voltage connections from ECG lead wires to be at least 8 millimeters apart. Hence, accommodating (10) resistors that are each located within a high voltage portion of a pathway 130 can require occupation of a substantial portion of space provided by a circuit board 230 including the low voltage electronics.

Instead, in accordance with the invention, a resistor 220 is located (electrically connected) within the rear conductive pathway 126 and also located substantially away from the circuit board 230 and other low voltage electronics. Preferably, the resistor 220 is physically located within a cavity 232 that resides as a portion of the passageway 236. The cavity 232 is also referred to as a barrel recess 232. Optionally, the cavity 232 is dimensioned to accommodate a variety of resistor sizes. As a result, manufacture of the ECG monitoring apparatus 120 is flexible with respect to the selection of a particular resistor among various types and sources of resistors.

For example, if a first resistor supplier becomes unavailable, or can no longer supply a sufficient number of resistors or is no longer a supplier of choice, a second resistor supplier can be chosen even if the physical dimensions of the resistor supplied by the second resistor supplier differ from the physical dimensions of the resistor supplied by the first resistor supplier. Further, incorporation of the second resistor into the apparatus 120 does not force changes to other components of the apparatus 120.

The location of the resistor 220 within the rear conductive (electronics side) path 126 and not within the front conductive (patient side) path 122, causes the higher voltage portion of the combined conductive pathway 130 to reside within the apparatus 120. The lower 126a and upper carriers 126b provide galvanic isolation and mechanical support to the higher voltage portion of the combined conductive pathway 130.

Figure 3A:
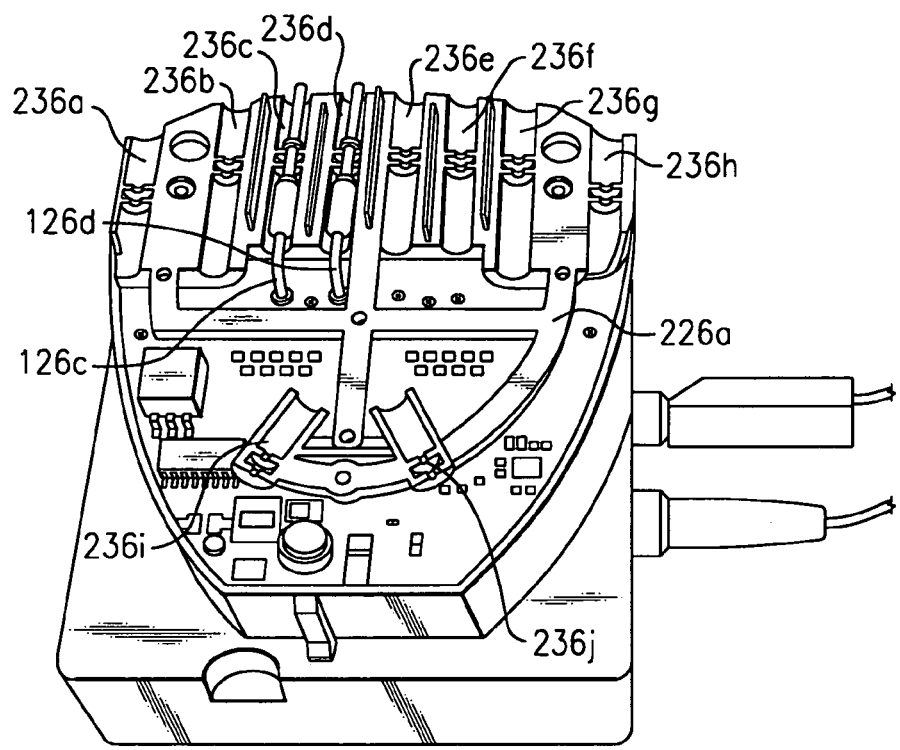
FIG. 3A is top perspective view of a lower carrier of FIG. 2 with reference numbers identifying portions of passageways.

FIG. 3A is top perspective view of the lower carrier 226a of FIG. 2 with reference numbers identifying portions of passageways 236a-236h within the ECG monitoring apparatus 120 of FIG. 2. As shown, the lower carrier 226a is manufactured from injection molded plastic and includes indentations 236a-236h that each define a lower portion of each of the (8) lower front passageways 236a-236h and each of the (2) rear passageways 236i-236j. The lower portion and an upper portion of each of the passageways 236a-236j are formed by stacking (abutting) the upper carrier 226b on top of the lower 226a carrier. The upper portion of each of the (10) passageways 236a-236j is included within the lower surface of the upper carrier 226b (See FIG. 3C).

As shown, passageways 236c and 236d each include electrical components that are connected to form rear conductive pathways 126c and 126d respectively as also shown in FIG. 2. Each of the conductive pathways 126c-126d are constructed from the connection of a contact pin 224, a base 222, a resistor 220 and a conductor 218 as described in association with FIG. 2. Preferably, other rear conductive pathways 126, like that described in association with FIG. 2, are included within all of the passageways 236a-236j.

Figure 3B:
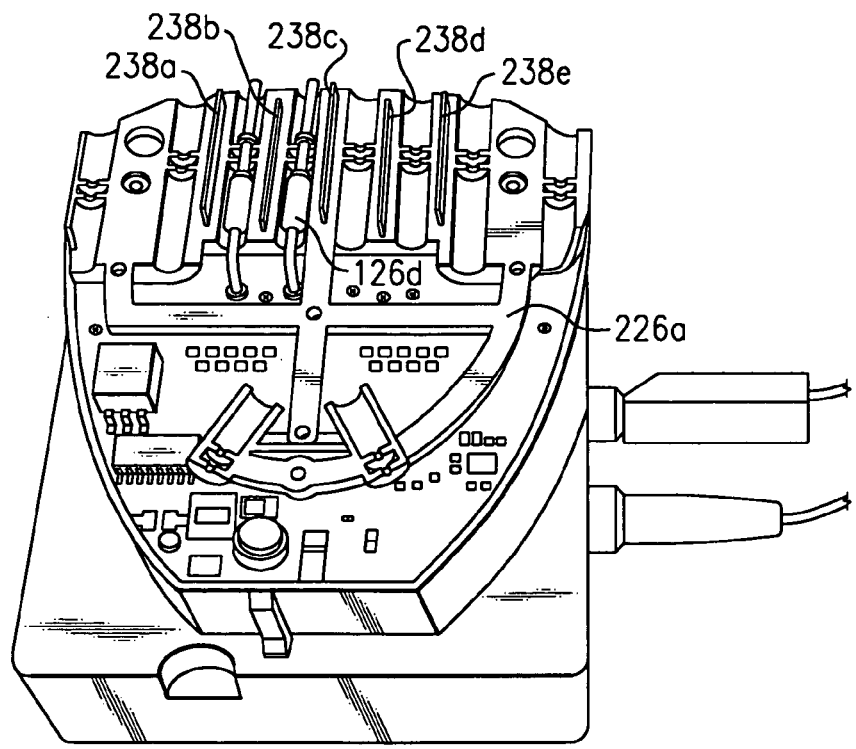
FIG. 3B is top perspective view of the lower carrier of FIG. 2 with reference numbers identifying portions of baffles.

FIG. 3B is top perspective view of the lower carrier 226a of FIG. 2 with reference numbers identifying portions of (5) baffles 238a-238e. As shown, the lower carrier 226a also includes a lower portion of each of (5) baffles 238a-238e in addition to the lower portion of each of the (10) passageways 236a-236j. The baffles 238a-238e are each located in between adjacent pairs of front lower passageways 236b-236g. The baffles 238a-238e are configured to provide additional galvanic isolation between pairs of adjacent passageways 236b-236g that are located at distances closer to each other than distances between pairs of other passageways including 236a, 236h, 236i-236j. The passageways 236a, 236h, 236i-236j are cylinder shaped and do not require a baffle.

Each of the (4) lower front passageways 236c-236f are disposed between two of the (5) baffles 238a-238e. For example, passageway 236c is disposed between baffles 238a and 238b and passageway 236d is disposed between 238b and 238c and passageway 236f is disposed between 238d and 238e. An upper portion of each of the (10) front and rear passageways 236a-236j and an upper portion of each of the (5) baffles 238a-238e is provided by the lower surface of the upper carrier 226b (See FIG. 3C).

Figure 3C:
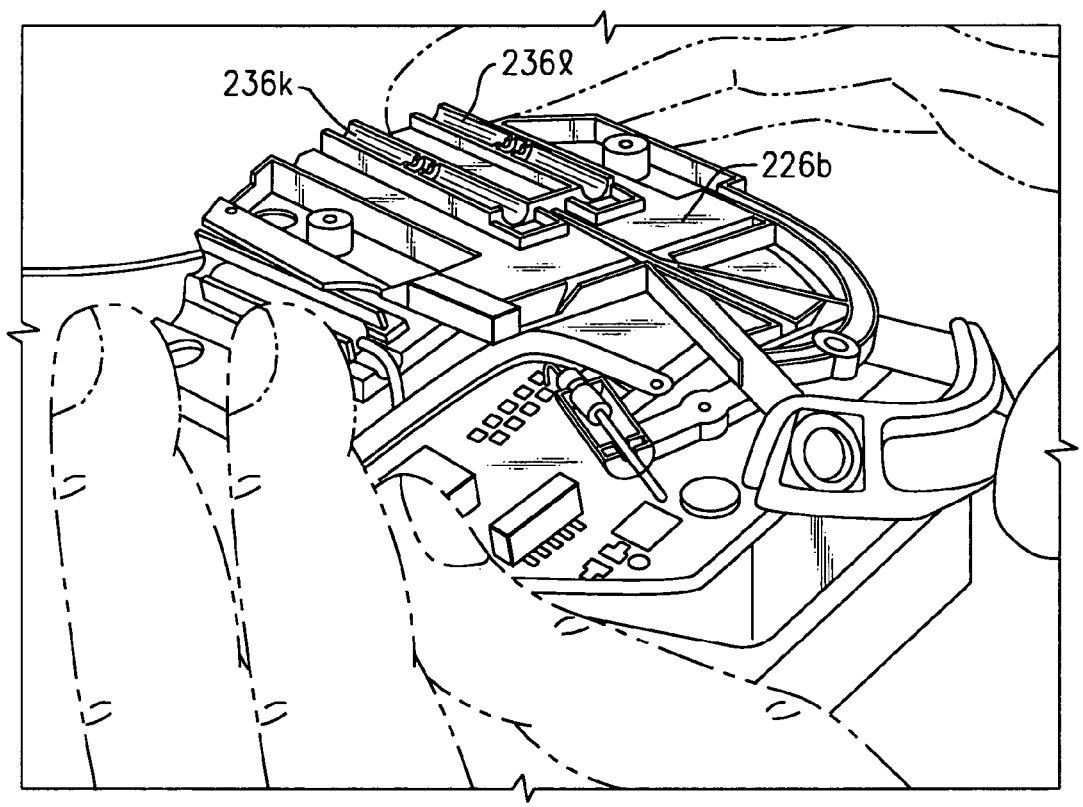
FIG. 3C is top perspective view of an upper carrier of the ECG monitoring apparatus of FIG. 2.

FIG. 3C is top perspective view of an upper carrier 226b of the ECG monitoring apparatus 120 of FIG. 2. As shown in this embodiment, the upper carrier 226b is manufactured from injection molded plastic and is configured (shaped) to stack (abut) on top of the lower carrier 226a. The bottom side (not shown) of the upper carrier 226b includes an upper portion of each of the (8) lower front passageways 236a-236h and an upper portion of each of the (2) rear passageways 236i-236j, an upper portion of each of (5) front baffles 238a-238e. The top side of the upper carrier 226b includes the additional (2) upper front passageways 236k-236l which are bounded from above by the outer surface 140 of the apparatus 120 (See FIG. 1B). Each of the additional (2) upper front passageways 236k-236l provide passage for audio cables (not shown).

When stacked on top of the lower carrier 226a, the upper carrier 226b completes the formation of the lower front (8) passageways 236a-236h, the formation of the (2) rear passageways 236i-236j and the formation of the (5) front baffles 238a-238e.

The invention can be applied to various types of devices that include low voltage electronics and that can be damaged from outside electrical sources. This is particularly applicable to low voltage electronics having an electrical connection to a conductive path that can make unwanted contact with outside sources of electrical energy.

For example, medical devices that are configured to receive signals from wire connected pressure and/or thermal transducers, can be vulnerable from voltage surges from outside electrical sources. Also for example, other devices monitoring EKG signals (brainwaves), cardiac output, blood pressure or other physiological data from a patient can be vulnerable to unwanted contact and damage from electrical sources of high voltage.

Besides a defibrillator, there are many other electrical sources of voltage within proximity to a patient within a health care environment that can potentially create a high voltage contact with devices that include low voltage electronics. For example, electrical cutting tools used for surgery on a patient, or electrical thermal devices that apply heat to a patient, are likely sources of high voltage. Operation of these types of tools may cause an unwanted transfer of electrical energy to other devices that include low voltage electronics and that are located in proximity to a patient. Devices that simply draw line voltage from a standard electrical outlet, such as a lamp, can possible cause unwanted transfer of electrical energy to other devices that include low voltage electronics and that are located in proximity to a patient.

While the present invention has been explained with reference to the structure disclosed herein, it is not confined to the details set forth and this invention is intended to cover any modifications and changes as may come within the scope and spirit of the following claims.

What is claimed is:

1. A medical apparatus that is configured for providing compact storage of, and electrical isolation between, each of a plurality of signal conductive pathways, comprising:
   a front conductive pathway that includes a first and a second end, said first end is configured to receive electrical signals that are associated with a patient, said second end is configured to make electrical contact with a first end of a rear conductive pathway, said front conductive pathway is detachable from and re-attachable to said rear conductive pathway via an electrical connection that is substantially enclosed within a housing;
   said rear conductive pathway includes a second end that is configured to make electrical contact with electronics that are configured to process said electrical signals, said rear conductive pathway includes a resistor that is located between said first end and said second end of said rear conductive pathway and that is configured to protect said electronics from damaging effects of a voltage surge that could travel through said front conductive pathway and into said rear conductive pathway; and where
   said housing includes an outer surface that substantially encloses said electrical connection and that provides substantial protection of said electrical connection from electrical contact resulting from physical contact with an object that is located outside of said housing.

2. The apparatus of claim 1 where said front conductive pathway excludes a resistor that is configured to protect said electronics from damaging effects of a voltage surge traveling through said front conductive pathway.

3. The apparatus of claim 1 where internal structures that are substantially enclosed within said housing are configured to electrically isolate said electrically conductive pathway segment from other electrically conductive pathways that are located outside of said passageway.

4. The apparatus of claim 3 where said apparatus includes a plurality of front conductive pathways and where said housing includes a plurality of said passageways and where each of said plurality of said passageways enclose an instance of said conductive pathway segment including said portion of each said front conductive pathway and a portion of a respective and separate rear conductive pathway.

5. The apparatus of claim 4 where each of said plurality of passageways is bounded by insolating structures within said housing which are configured to electrically isolate each said conductive pathway segment that is located within each said passageway from another conductive pathway segment that is located within another passageway residing within said housing.

6. The apparatus of claim 4 where said isolating structures are implemented as plastic baffles that are located between said pairs of said plurality of passageways.

7. The apparatus of claim 6 where said plastic baffles are manufactured via injection molding.

8. The apparatus of claim 3 where a contact pin is attached to said first end of said rear conductive pathway and mechanically supported in a stationary position within said passageway.

9. The apparatus of claim 8 where said contact pin includes a longitudinal axis and a flat surface that is substantially parallel to said longitudinal axis, said flat surface is configured to correctly orient and seat said contact pin within a recess within said passageway, said recess includes a flat interior surface that is configured to mate with said flat surface of said contact pin.

10. The apparatus of claim 8 where a patient lead electrode is configured to make electrical contact with said first end of said front conductive pathway and where said second end of said front conductive pathway is configured to make electrical contact with said contact pin.

11. The apparatus of claim 10 where said second end of said front conductive pathway is configured as a female type of electrical connector.

12. The apparatus of claim 3 where said passageway includes a barrel recess that provides a void within which said resistor of said rear conductive pathway is located.

13. The apparatus of claim 12 where said barrel recess is configured to accommodate a variety of resistor sizes that are configured to protect said electronics from damaging effects of a voltage surge.

14. The apparatus of claim 1 where said voltage surge is generated from a defibrillation shock.

15. The apparatus of claim 1 where said electronics includes a printed circuit board (PCB) and where said second end is electrically connected to said PCB.

16. The apparatus of claim 15 where said PCB includes a passageway and where a portion of said rear conductive pathway is disposed within said passageway.

17. The apparatus of claim 1 where said apparatus is configured to function as an electro-cardiogram (ECG) monitoring device and said signals are ECG signals.

18. The apparatus of claim 1 where said apparatus is configured receive signals from a transducer.

19. An ECG monitoring apparatus that is configured for providing compact storage of, and electrical isolation between, each of a plurality of ECG lead wires, comprising:
   a lead wire that includes a first and a second end, said first end is configured to receive electrical signals that are associated with a patient, said second end is configured to make electrical contact with a first end of a rear conductive pathway, said lead wire is detachable from and re-attachable to said rear conductive pathway via an electrical connection that is disposed within an enclosure;
   said rear conductive pathway includes a second end that is configured to make electrical contact with electronics that are configured to process said electrical signals, said rear conductive pathway includes a resistance that is located between said first end and said second end of said rear conductive pathway and that is configured to protect said electronics from damaging effects of a voltage surge that could travel through said lead wire and into said rear conductive pathway; and where said enclosure includes an outer surface that substantially encloses said electrical connection and that provides substantial protection of said electrical connection from electrical contact resulting from physical contact with an object that is located outside of said enclosure.

20. An method for providing compact storage of, and electrical isolation between, each of a plurality of ECG signal conductive pathways, comprising the steps of:

providing a front conductive pathway and a rear conductive pathway, said front conductive pathway includes a first and a second end, said first end is configured to receive ECG signals from a patient, said second end is configured to make electrical contact with a first end of said rear conductive pathway, said front conductive pathway is detachable from and re-attachable to said rear conductive pathway via an electrical connection that is substantially enclosed within a housing; and where said rear conductive pathway includes a second end that is configured to make electrical contact with electronics that are configured to process said ECG signals, said rear conductive pathway includes a resistor that is located between said first end and said second end of said rear conductive pathway and that is configured to protect said electronics from damaging effects of a voltage surge traveling through said front conductive pathway and into said rear conductive pathway; and where said housing includes an outer surface that substantially encloses said electrical connection and that provides substantial protection of said electrical connection from electrical contact resulting from physical contact with an object that is located outside of said housing.

* * * * *